(12) United States Patent
Mori et al.

(10) Patent No.: US 11,510,623 B2
(45) Date of Patent: Nov. 29, 2022

(54) PATCHABLE BIOSENSOR

(71) Applicant: NITTO DENKO CORPORATION, Ibaraki (JP)

(72) Inventors: Shigeyasu Mori, Ibaraki (JP); Ryoma Yoshioka, Ibaraki (JP); Eiji Toyoda, Ibaraki (JP); Keiji Takemura, Ibaraki (JP)

(73) Assignee: NITTO DENKO CORPORATION, Ibaraki (JP)

( * ) Notice: Subject to any disclaimer, the term of this patent is extended or adjusted under 35 U.S.C. 154(b) by 117 days.

(21) Appl. No.: 16/762,319

(22) PCT Filed: Oct. 25, 2018

(86) PCT No.: PCT/JP2018/039750
§ 371 (c)(1),
(2) Date: May 7, 2020

(87) PCT Pub. No.: WO2019/093144
PCT Pub. Date: May 16, 2019

(65) Prior Publication Data
US 2020/0289058 A1 Sep. 17, 2020

(30) Foreign Application Priority Data
Nov. 10, 2017 (JP) .............................. JP2017-217040

(51) Int. Cl.
*A61B 5/00* (2006.01)
*A61B 5/01* (2006.01)
(Continued)

(52) U.S. Cl.
CPC .............. *A61B 5/6833* (2013.01); *A61B 5/01* (2013.01); *A61B 5/021* (2013.01);
(Continued)

(58) Field of Classification Search
CPC .................................................... A61B 5/6833
See application file for complete search history.

(56) References Cited

U.S. PATENT DOCUMENTS

| 5,483,967 A | 1/1996 | Ohtake |
| 6,416,471 B1 | 7/2002 | Kumar et al. |

(Continued)

FOREIGN PATENT DOCUMENTS

| CN | 204246122 U | 4/2015 |
| CN | 207286046 U | 5/2018 |

(Continued)

OTHER PUBLICATIONS

Extended European Search Report issued for corresponding European Patent Application No. 18876597.8 dated Jun. 24, 2021.
(Continued)

*Primary Examiner* — Gary Jackson
*Assistant Examiner* — Zahed Kabir
(74) *Attorney, Agent, or Firm* — Hauptman Ham, LLP

(57) ABSTRACT

A patchable biosensor includes a substrate extending in a longitudinal direction and being stretchable for being patched to a surface of a living body and an electronic component disposed on a one-side surface in a thickness direction of the substrate and extending in the longitudinal direction. The longitudinal direction of the electronic component crosses the longitudinal direction of the substrate.

3 Claims, 13 Drawing Sheets

(51) Int. Cl.
  *A61B 5/0205* (2006.01)
  *A61B 5/021* (2006.01)
  *A61B 5/024* (2006.01)
  *A61B 5/259* (2021.01)
  *A61B 5/291* (2021.01)
  *A61B 5/296* (2021.01)

(52) U.S. Cl.
  CPC ....... *A61B 5/02055* (2013.01); *A61B 5/02438* (2013.01); *A61B 5/259* (2021.01); *A61B 5/291* (2021.01); *A61B 5/296* (2021.01); *A61B 2562/0219* (2013.01)

(56) References Cited

U.S. PATENT DOCUMENTS

| | | | |
|---|---|---|---|
| 2005/0197540 A1 | 9/2005 | Liedtke | |
| 2006/0030781 A1 | 2/2006 | Shennib | |
| 2007/0191728 A1* | 8/2007 | Shennib | A61B 5/389 128/903 |
| 2008/0091090 A1* | 4/2008 | Guillory | A61B 5/4094 600/301 |
| 2008/0275327 A1* | 11/2008 | Faarbaek | A61B 5/68335 600/382 |
| 2009/0076397 A1* | 3/2009 | Libbus | A61B 5/259 600/509 |
| 2013/0096401 A1 | 4/2013 | Lash et al. | |
| 2013/0226018 A1 | 8/2013 | Kumar et al. | |
| 2015/0043176 A1 | 2/2015 | Ahn | |
| 2015/0351689 A1 | 12/2015 | Adams et al. | |
| 2016/0162774 A1 | 6/2016 | Mei et al. | |
| 2017/0223846 A1* | 8/2017 | Elolampi | H05K 1/189 |
| 2017/0244543 A1* | 8/2017 | Raj | H04L 67/04 |

FOREIGN PATENT DOCUMENTS

| | | |
|---|---|---|
| JP | H6-245915 A | 9/1994 |
| JP | 2002-541893 A | 12/2002 |
| JP | 2007-180197 A | 7/2007 |
| JP | 2012-10978 A | 1/2012 |
| JP | 2016-508396 A | 3/2016 |
| JP | 2018-164725 A | 10/2018 |
| KR | 101048662 B1 * | 5/2010 |
| WO | 2017/144710 A1 | 8/2017 |

OTHER PUBLICATIONS

International Search Report issued in corresponding International Patent Application No. PCT/JP2018/039750 dated Jan. 29, 2019, along with an English translation, citing above references.

Written Opinion issued in corresponding International Patent Application No. PCT/JP2018/039750 dated Jan. 29, 2019, citing above references.

Office Action dated Feb. 11, 2022, for corresponding Taiwanese Patent Application No. 107138403, along with an English translation.

Office Action dated May 13, 2022 for corresponding Taiwanese Patent Application No. 107138403, along with an English translation.

Office Action dated Jul. 19, 2022 for corresponding Japanese Patent Application No. 2019-552709, along with an English machine translation (11 pages).

Office Action dated Oct. 11, 2022 for corresponding Japanese Patent Application No. 2019-552709, along with an English machine translation (12 pages).

* cited by examiner

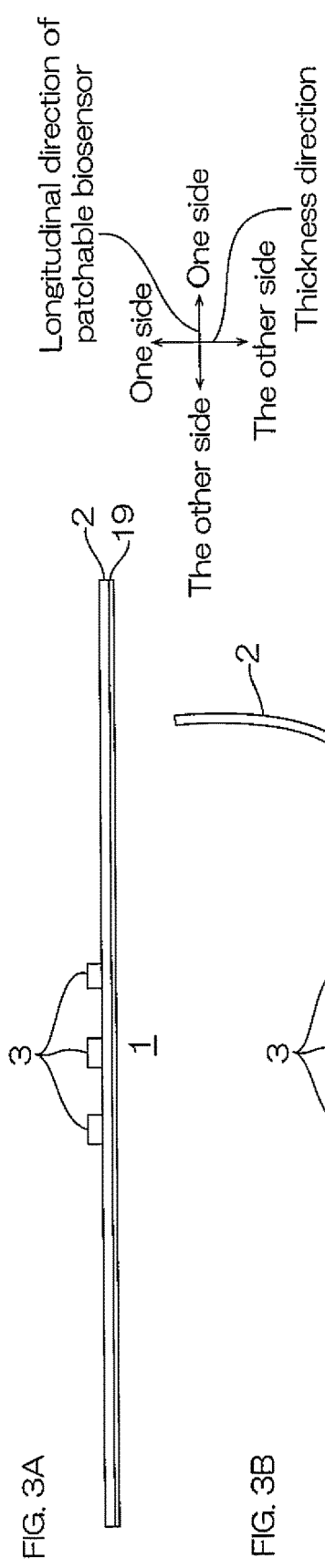
FIG. 3A
FIG. 3B
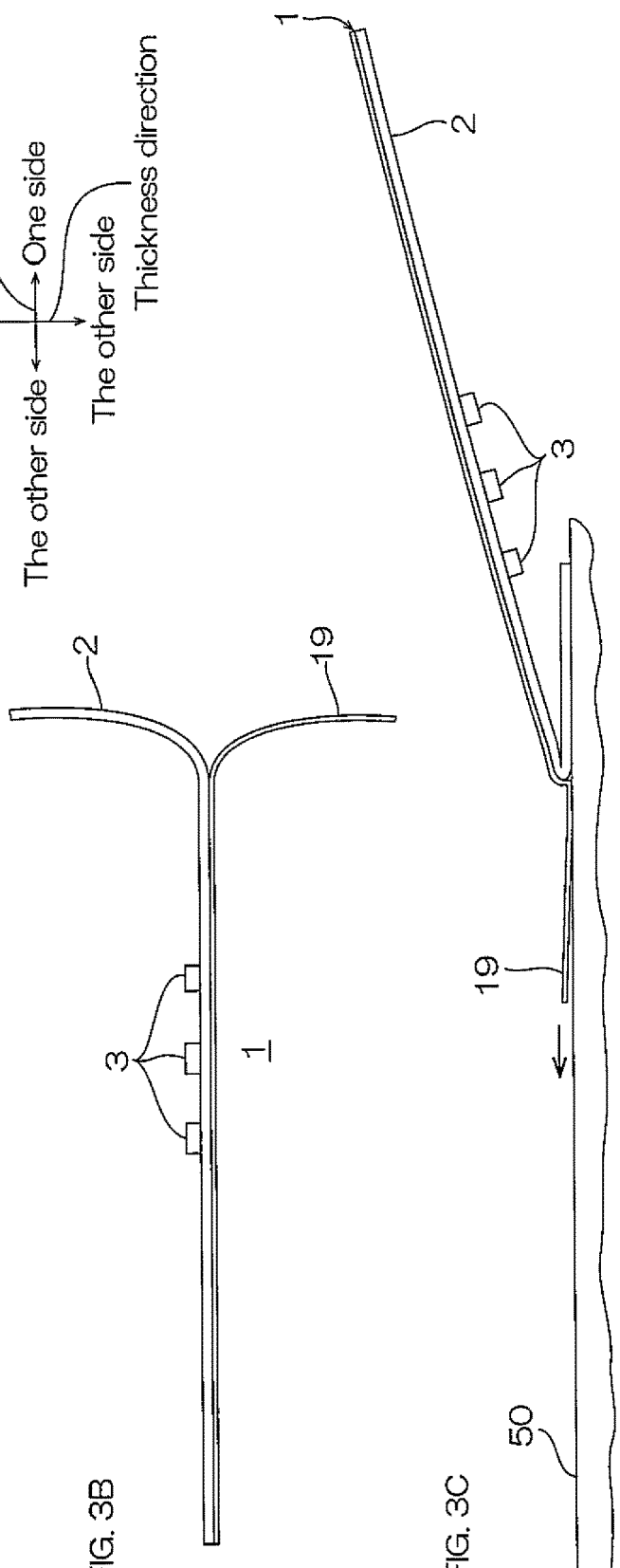
FIG. 3C
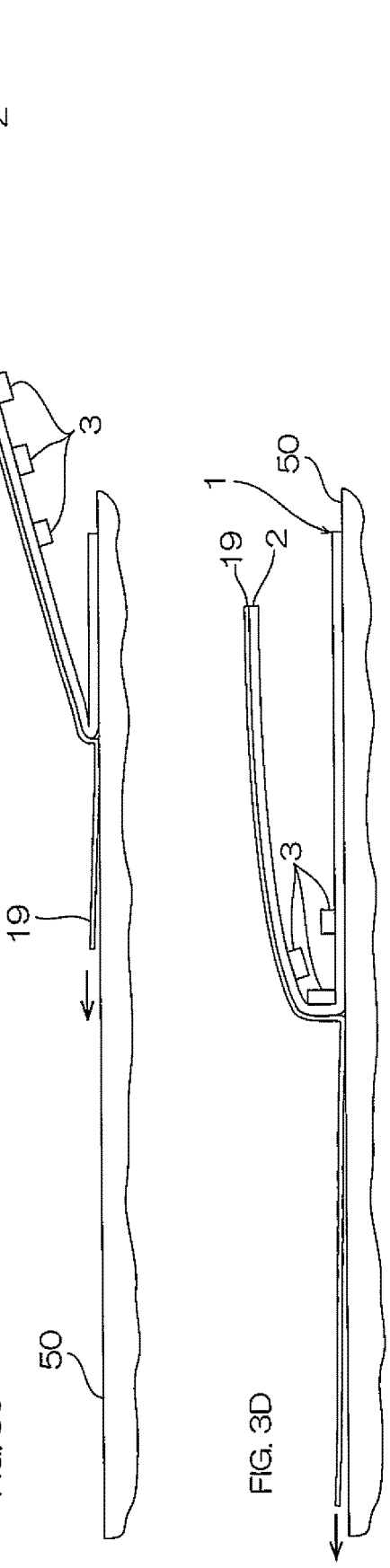
FIG. 3D

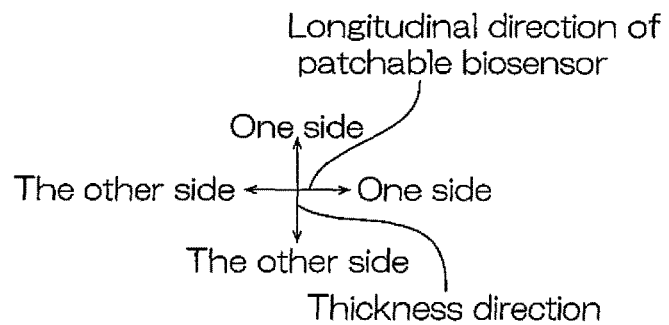
FIG. 5A
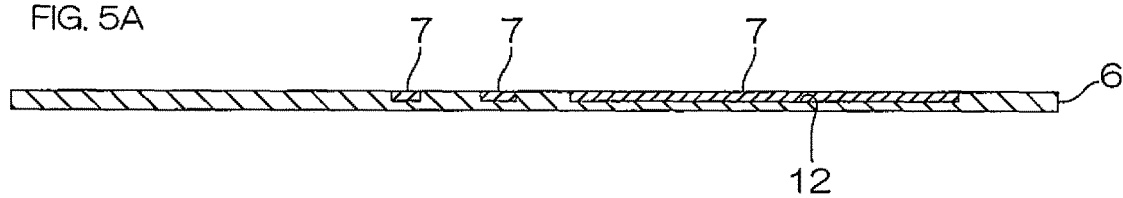
FIG. 5B
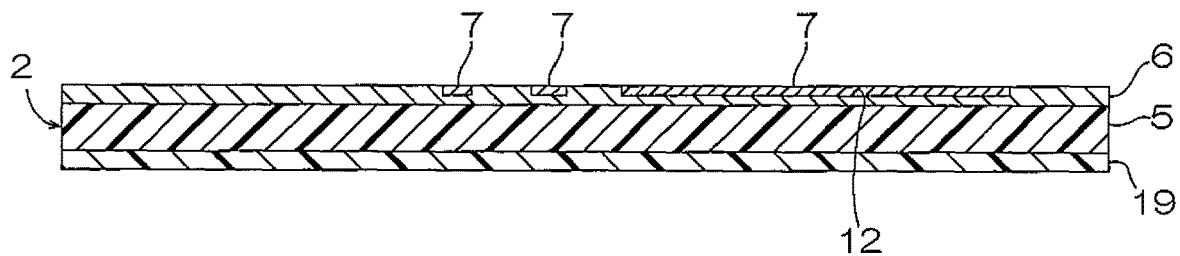
FIG. 5C
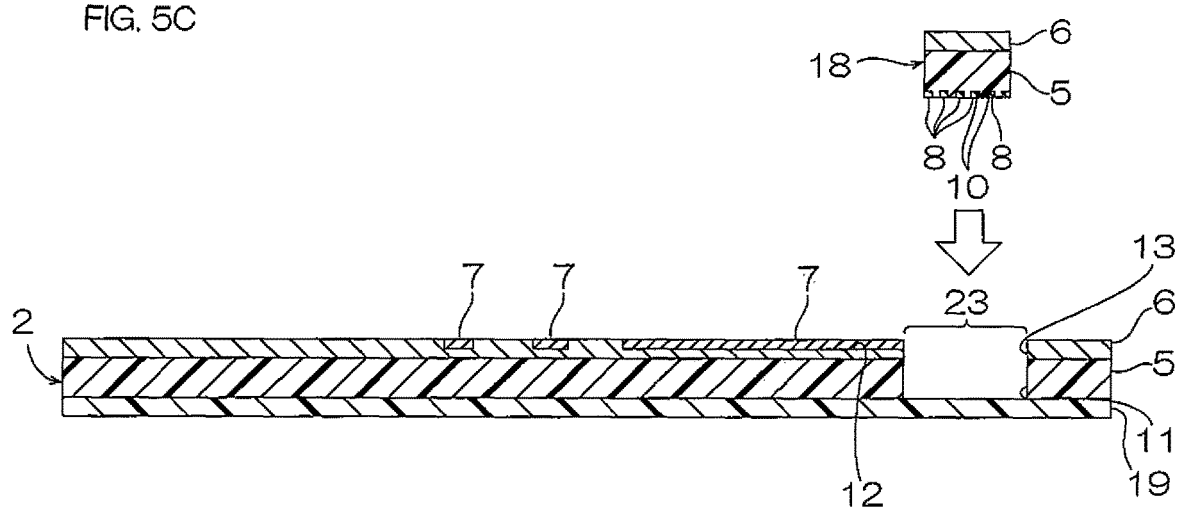
FIG. 5D
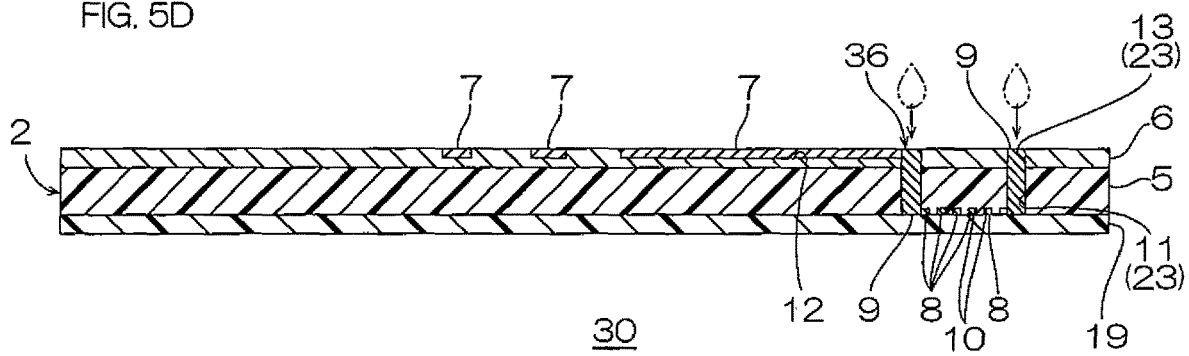

FIG. 7
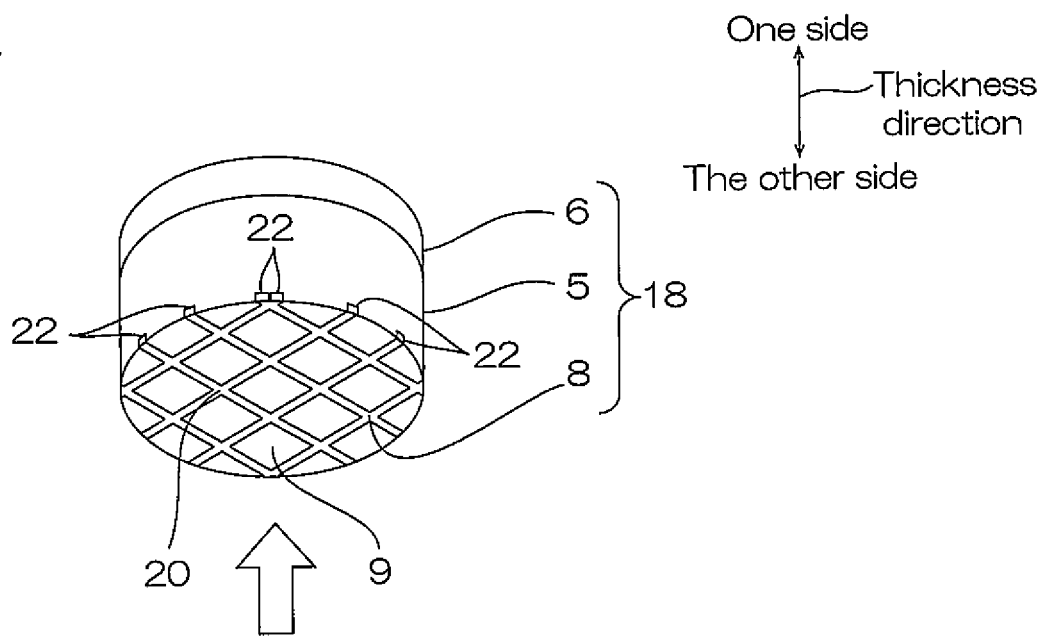
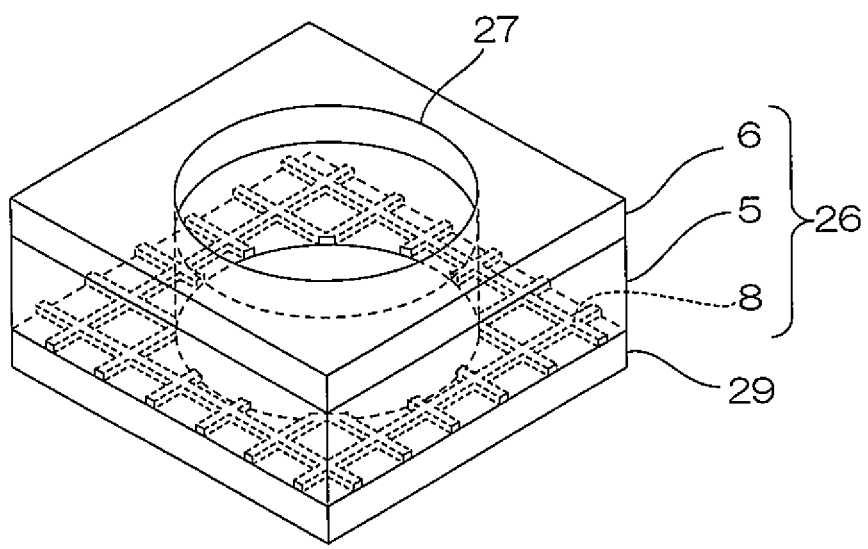

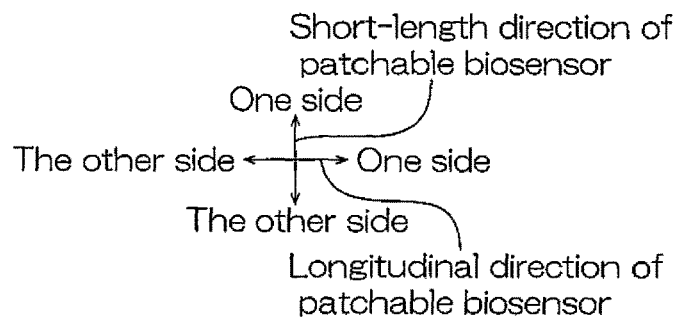
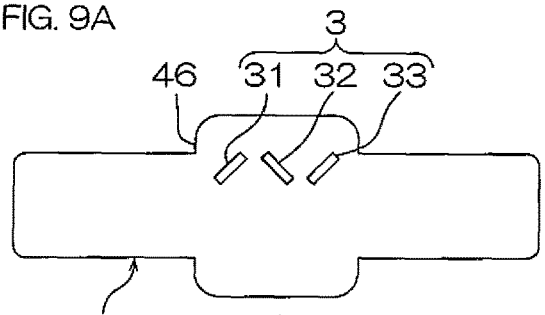
FIG. 9A
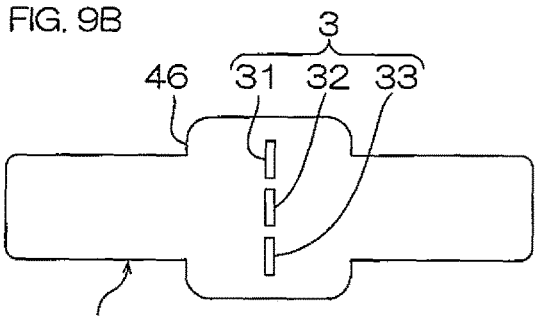
FIG. 9B
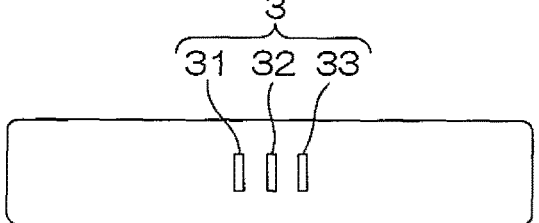
FIG. 9C
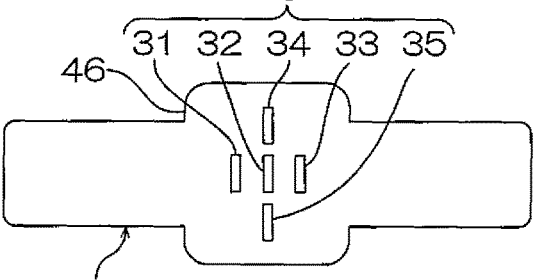
FIG. 9D
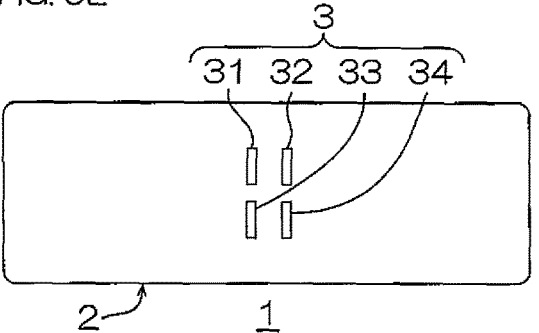
FIG. 9E
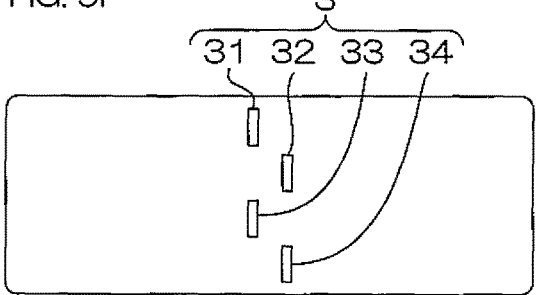
FIG. 9F
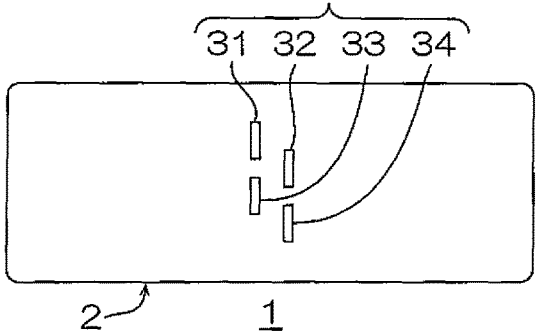
FIG. 9G
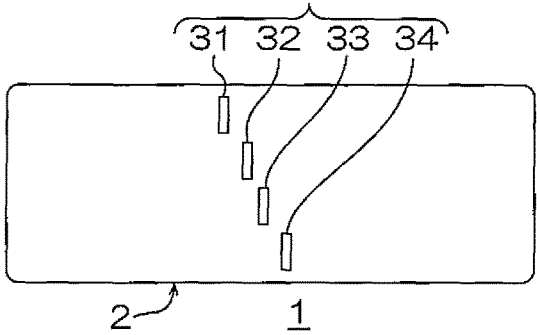
FIG. 9H

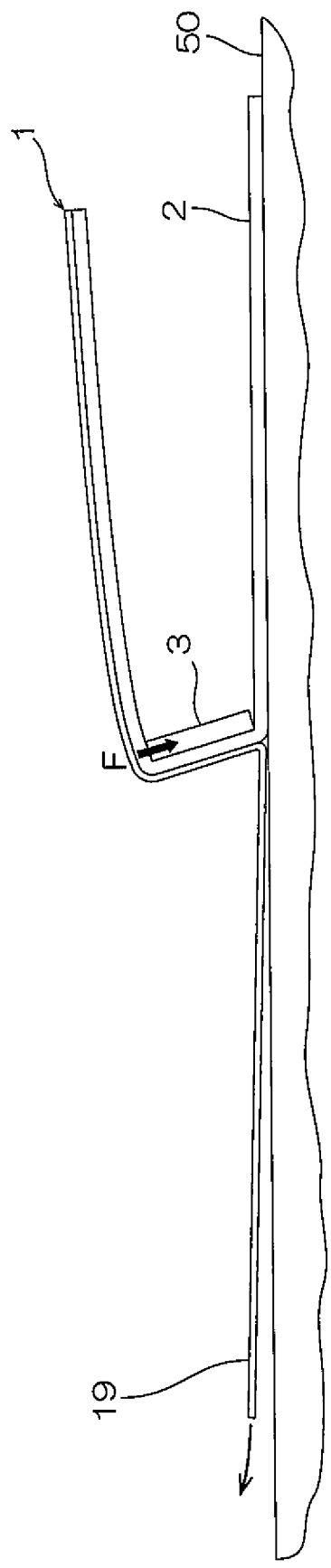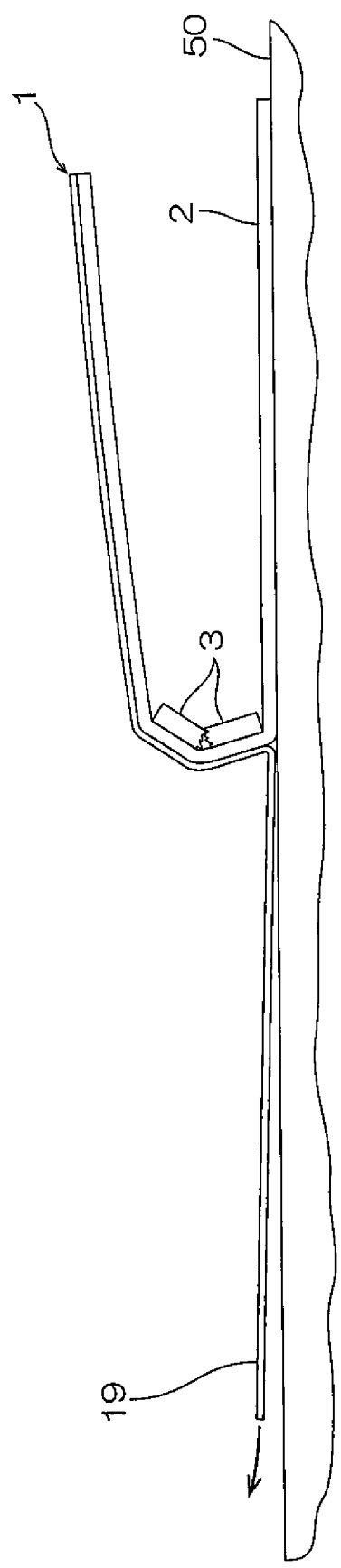

PATCHABLE BIOSENSOR

CROSS REFERENCE TO RELATED APPLICATION

This application claims the priority of Japanese Patent Application No. 2017-217040, filed on Nov. 10, 2017, in the JPO (Japanese Patent Office). Further, this application is the National Phase Application of International Application No. PCT/JP2018/039750, filed on Oct. 25, 2018, which designates the United States and was published in Japan. Both of the priority documents are hereby incorporated by reference in their entireties.

TECHNICAL FIELD

The present invention relates to a patchable biosensor.

BACKGROUND ART

Conventionally, a biocompatible polymer board that is capable of being patched to the skin of a person or the like has been known.

For example, a biocompatible polymer board including a polymer layer that extends in a longitudinal direction and has flexibility and a module for data acquisition that is fixed to a one-side surface thereof has been proposed (ref: for example, Patent Document 1).

CITATION LIST

Patent Document

Patent Document 1: Japanese Unexamined Patent Publication No. 2012-10978

SUMMARY OF THE INVENTION

Problem to be Solved by the Invention

In the biocompatible polymer board of the above-described Patent Document 1, the module for data acquisition extends long in the same direction as the longitudinal direction of the polymer layer. Thus, when the biocompatible polymer board of the above-described Patent Document 1 is patched to the skin of a person along the longitudinal direction of the polymer layer, deformation such as bending (or curving) along the longitudinal direction occurs in the polymer layer having flexibility. At this time, there is a disadvantage that a large stress is applied to the module for data acquisition caused by the deformation of the polymer layer, so that the module for data acquisition is damaged.

The present invention provides a patchable biosensor that is capable of suppressing damage to an electronic component when a substrate is patched to a surface of a living body.

Means for Solving the Problem

The present invention (1) includes a patchable biosensor including a substrate extending in a longitudinal direction and being stretchable for being patched to a surface of a living body and an electronic component disposed on a one-side surface in a thickness direction of the substrate and extending in the longitudinal direction, wherein the longitudinal direction of the electronic component crosses the longitudinal direction of the substrate.

When the substrate is patched to the surface of the living body along the longitudinal direction thereof, and the substrate is deformed along the longitudinal direction thereof, in the patchable biosensor, the longitudinal direction of the electronic component crosses that of the substrate, so that a stress applied to the electronic component can be reduced. Thus, when the substrate is patched to the surface of the living body, damage to the electronic component can be suppressed.

The present invention (2) includes the patchable biosensor described in (1), wherein the longitudinal direction of the electronic component is perpendicular to the longitudinal direction of the substrate.

When the substrate is patched to the surface of the living body along the longitudinal direction thereof, and the substrate is deformed along the longitudinal direction thereof, in the patchable biosensor, the longitudinal direction of the electronic component is perpendicular to that of the substrate, so that the stress applied to the electronic component can be furthermore surely reduced. Thus, when the substrate is patched to the surface of the living body, the damage to the electronic component can be furthermore surely suppressed.

The present invention (3) includes the patchable biosensor described in (1) or (2) further including a release sheet disposed on an other-side surface in the thickness direction of the substrate and for being peeled along the longitudinal direction of the substrate.

When the release sheet is peeled along the longitudinal direction of the substrate, the substrate is stretchable, so that deformation easily occurs.

As described above, however, in the patchable biosensor, the longitudinal direction of the electronic component crosses that of the substrate, so that when the release sheet is peeled from the substrate, the stress applied to the electronic component can be reduced.

The present invention (4) includes the patchable biosensor described in any one of (1) to (3), wherein the electronic component includes at least the two electronic components disposed next to each other along the longitudinal direction of the substrate.

At least the two electronic components disposed that are next to each other may be brought into contact with each other to be damaged caused by the above-described deformation along the longitudinal direction of the substrate.

In the patchable biosensor, however, the longitudinal direction of the electronic component crosses that of the substrate, so that the above-described occurrence of the contact is suppressed, and the damage to the electronic component can be suppressed.

The present invention (5) includes the patchable biosensor described in (4), wherein a ratio (I/Tmax) of a gap I between the two electronic components in the longitudinal direction of the substrate to the maximum thickness Tmax of the electronic component is 2 or more.

The ratio (I/Tmax) of the gap I between the two electronic components in the longitudinal direction of the substrate to the maximum thickness Tmax of the electronic component is 2 or more, so that the contact of the two electronic components with each other is effectively suppressed, and the damage to the electronic component can be effectively suppressed.

The present invention (6) includes the patchable biosensor described in any one of (1) to (5), wherein the electronic component is at least one selected from the group consisting of an analog front end, a microcomputer, a memory, an interposer, and a chip.

In the patchable biosensor, at least one selected from the group consisting of the analog front end, the microcomputer, the memory, the interposer, and the chip is hard or fragile, and thus, the electronic component may be damaged when the stress is applied thereto.

As described above, however, in the patchable biosensor, the longitudinal direction of the electronic component crosses that of the substrate, so that the stress applied to the electronic component can be reduced.

Furthermore, the electronic component is at least one selected from the group consisting of the analog front end, the microcomputer, the memory, the interposer, and the chip, so that sensing performance of the patchable biosensor can be improved by the operation thereof.

Effect of the Invention

The patchable biosensor can suppress damage to an electronic component when a substrate is patched to a surface of a living body.

BRIEF DESCRIPTION OF THE DRAWINGS

FIGS. 3A to 3D show side views for illustrating a method for patching the patchable biosensor shown in FIGS. 1 and 2 to the skin and a state of applying a stress to an electronic component:

FIG. 3A illustrating a step of preparing the patchable biosensor,

FIG. 3B illustrating a step of peeling a portion of a first release sheet from a substrate and exposing a portion of the substrate, FIG. 3C illustrating a step of allowing a portion of the substrate to pressure-sensitively adhere to the skin, and FIG. 3D illustrating a state of applying the stress to the electronic component.

FIGS. 5A to 5D show production process views of a substrate in the patchable biosensor shown in FIG. 2:

FIG. 5A illustrating a step of preparing a substrate layer and a wire layer,

FIG. 5B illustrating a step of attaching a pressure-sensitive adhesive layer to the substrate layer, FIG. 5C illustrating a step of forming an opening portion and preparing a probe member, and FIG. 5D illustrating a step of fitting the probe member to the opening portion and a step of forming a connecting portion.

FIG. 7 shows perspective views for illustrating a production step of a probe member:

The upper-side view illustrating a perspective view when viewed from the other side in a thickness direction and The lower-side view illustrating a perspective view when viewed from one side in the thickness direction.

Figure 8A:
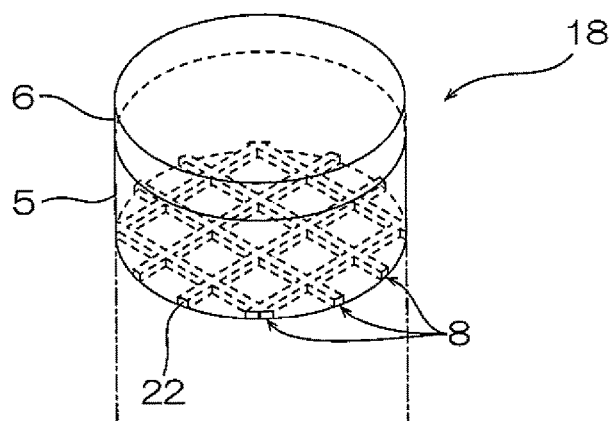
Figure 8B:
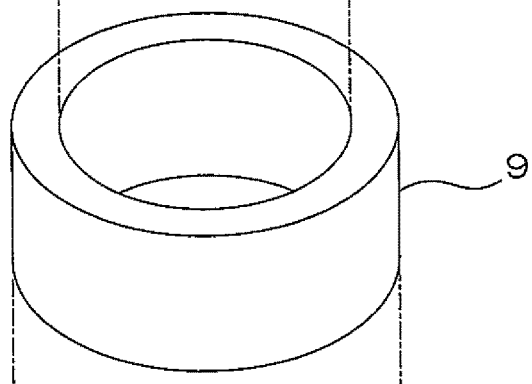
Figure 8C:
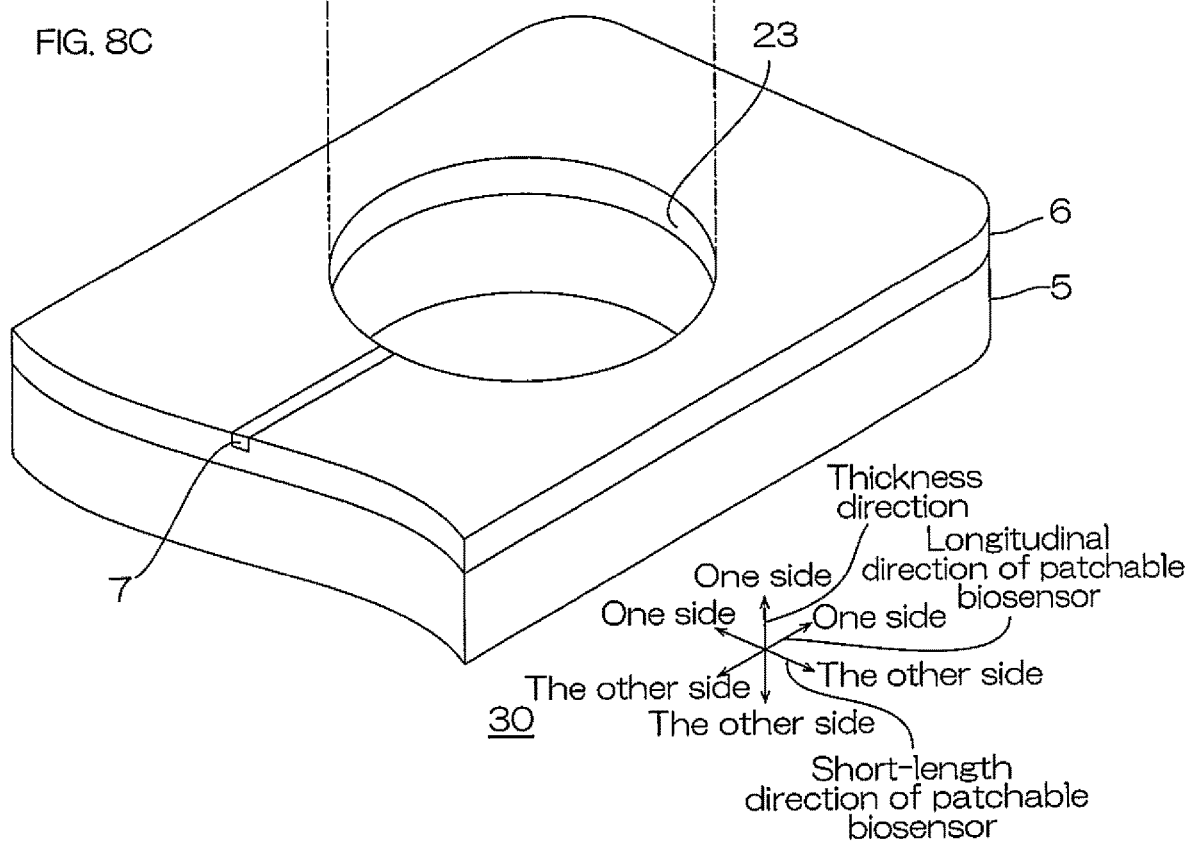

FIGS. 8A to 8C show disassembled perspective views of a probe member:

FIG. 8A illustrating a probe member,

FIG. 8B illustrating a connecting portion, and

FIG. 8C illustrating an opening portion in one end portion in a longitudinal direction of a substrate.

FIGS. 9A to 9H show modified examples of a patchable biosensor.

Figure 10:
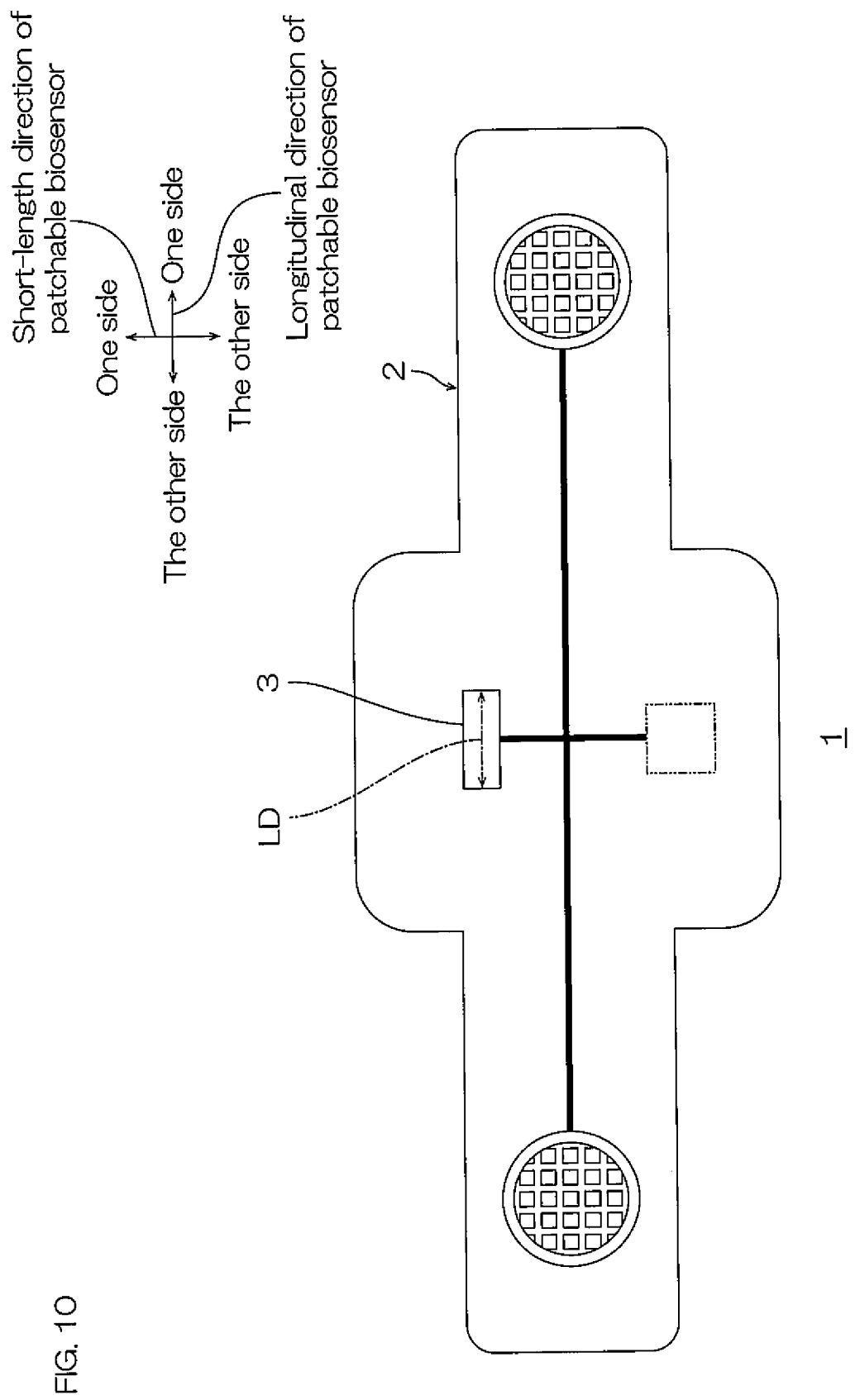

FIG. 10 shows a plan view of a patchable biosensor of Comparative Example 1 in which a longitudinal direction of an electronic component is along the longitudinal direction of a substrate.

FIGS. 11A and 11B show side views for illustrating a state of applying a stress to an electronic component along a longitudinal direction of the patchable biosensor of Comparative Example 1 shown in FIG. 10:

FIG. 11A illustrating a state of applying the stress to the electronic component and FIG. 11B illustrating a state of damaging the electronic component by the stress.

Figure 12:
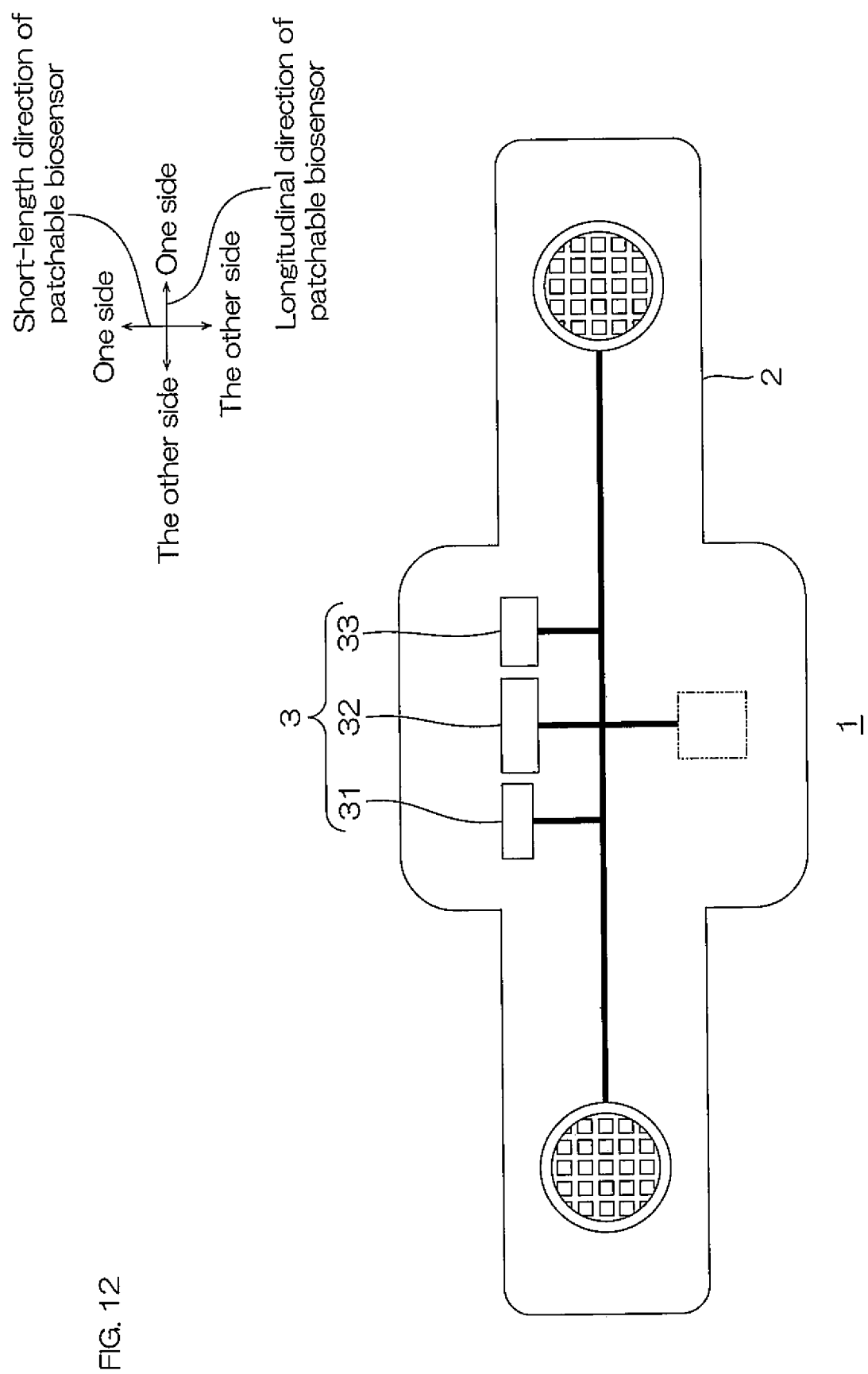

FIG. 12 shows a plan view of a patchable biosensor of Comparative Example 2 in which each of the longitudinal directions of a plurality of electronic components is along the longitudinal direction of a substrate.

Figure 13:
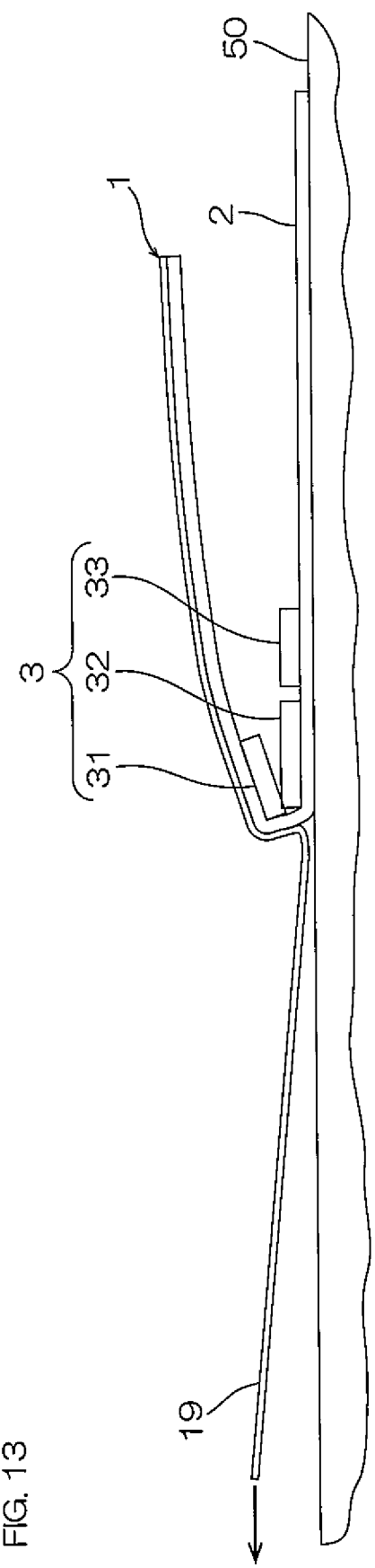

FIG. 13 shows a side view for illustrating a state in which electronic components next to each other are in contact with each other along the longitudinal direction of the patchable biosensor of Comparative Example 2 shown in FIG. 12.

DESCRIPTION OF EMBODIMENTS

A one embodiment of a patchable biosensor of the present invention is described with reference to FIGS. 1 to 4.

In FIGS. 3A to 3D, as described later, each layer (for example, a pressure-sensitive adhesive layer 5, a substrate layer 6, or the like) included in an electronic component 3 is omitted so as to clearly show a shape when viewed from the side of the electronic component 3.

Figure 1:
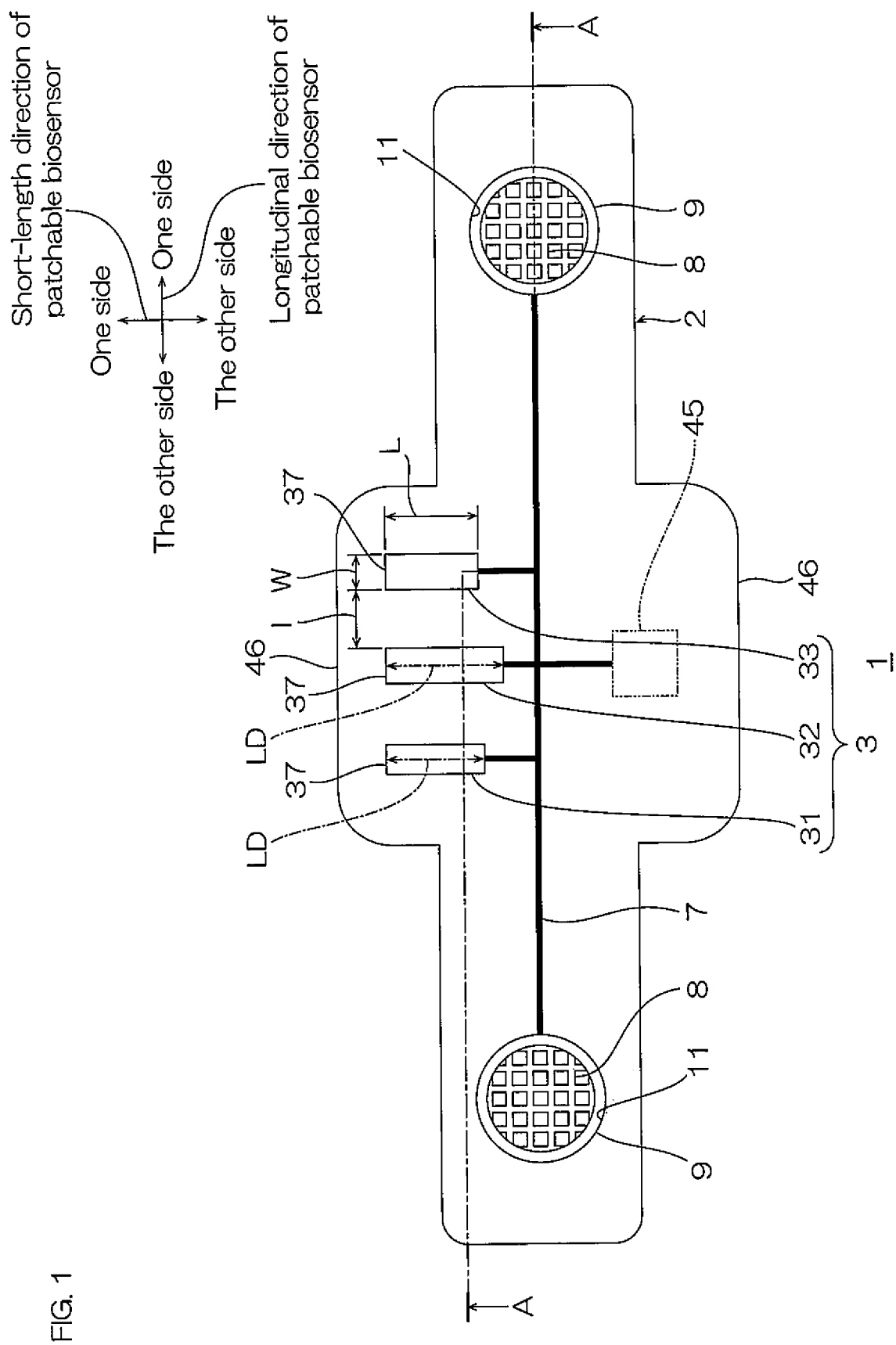
FIG. 1 shows a plan view of a one embodiment of a patchable biosensor of the present invention.
Figure 2:
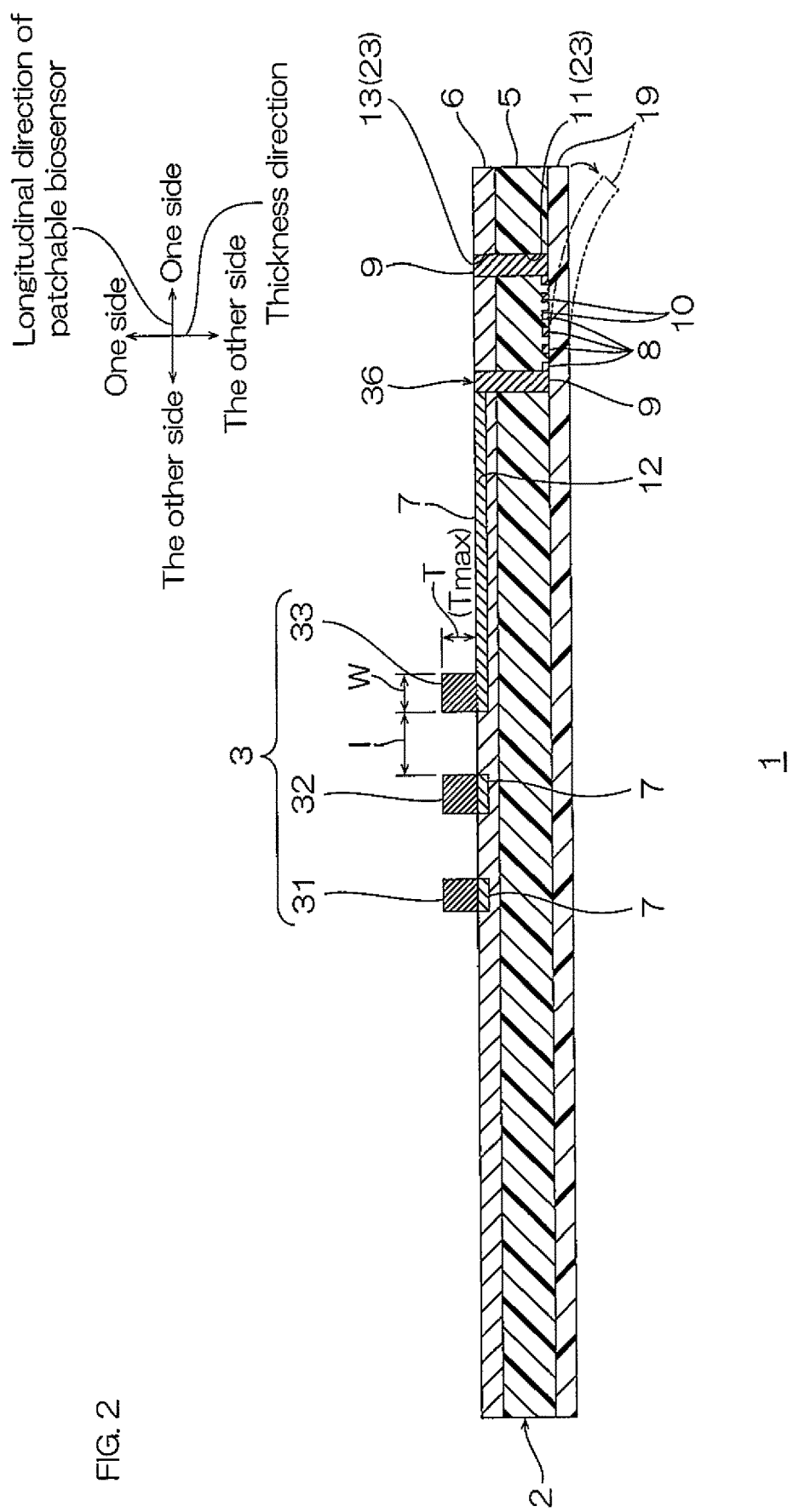
FIG. 2 shows a cross-sectional view along a longitudinal direction of the patchable biosensor shown in FIG. 1 and to be specific, shows a side cross-sectional view along an A-A line.

As shown in FIGS. 1 and 2, a patchable biosensor 1 has a generally flat plate shape extending in a longitudinal direction. The patchable biosensor 1 includes a substrate 2 and the electronic component 3 that is disposed on a one-side surface in a thickness direction of the substrate 2.

The substrate 2 is a patchable substrate including a circuit portion, and is also a substrate that is stretchable (flexible) and has pressure-sensitive adhesive properties, while having, for example, a circuit portion 36 (described later). The substrate 2 is a sheet that has a flat plate shape extending in the longitudinal direction and is excellently stretchable. To be specific, the substrate 2 has a belt shape extending in the longitudinal direction, and has a shape in which a central portion 46 in the longitudinal direction expands toward both outer sides in a short-length direction (direction perpendicular to the longitudinal direction and the thickness direction) (width direction).

The substrate 2 includes the pressure-sensitive adhesive layer 5, the substrate layer 6, a wire layer 7, a probe 8, and a connecting portion 9.

The pressure-sensitive adhesive layer 5 forms an other-side surface (pressure-sensitive adhesive surface) in the thickness direction of the substrate 2. That is, the pressure-sensitive adhesive layer 5 is a layer that imparts the pressure-sensitive adhesive properties to the other-side surface in the thickness direction of the patchable biosensor 1 so as to patch the substrate 2 to a surface of a living body (a skin 50 or the like in FIG. 4). The pressure-sensitive adhesive layer 5 forms the outer shape of the substrate 2. The pressure-sensitive adhesive layer 5 has a flat plate shape extending in the longitudinal direction.

The pressure-sensitive adhesive layer 5 has two first opening portions 11 in both end portions in the longitudinal direction thereof. Each of the two first opening portions 11 has a generally ring shape when viewed from the top. The first opening portion 11 passes through the pressure-sensitive adhesive layer 5 in the thickness direction. The other-side surface in the thickness direction at the inside of the first opening portion 11 has an opening toward the other side in the thickness direction and has a first groove 10 corresponding to the probe 8.

A material for the pressure-sensitive adhesive layer 5 is not particularly limited as long as it is, for example, a material having the pressure-sensitive adhesive properties. The pressure-sensitive adhesive layer 5 is also a stretchable material that is stretchable.

The substrate layer 6 forms the one-side surface in the thickness direction of the substrate 2. The substrate layer 6, along with the pressure-sensitive adhesive layer 5, forms the outer shape (shape when projected in the thickness direction) of the substrate 2. The shape when viewed from the top of the substrate layer 6 is the same as that when viewed from the top of the pressure-sensitive adhesive layer 5. The substrate layer 6 is disposed on the entire one-side surface in the thickness direction of the pressure-sensitive adhesive layer 5. The substrate layer 6 is a supporting layer that supports the pressure-sensitive adhesive layer 5. The substrate layer 6 has a flat plate shape extending in the longitudinal direction.

The substrate layer 6 has a second groove 12 corresponding to the wire layer 7 (described later) on the one-side surface in the thickness direction thereof. The second groove 12 has the same pattern shape as that of the wire layer 7 when viewed from the top. The second groove 12 has an opening toward one side in the thickness direction.

The substrate layer 6 has a second opening portion 13 corresponding to the first opening portion 11. The second opening portion 13 is communicated with the first opening portion 11 in the thickness direction. The second opening portion 13 has a generally ring shape when viewed from the top having the same shape and the same size as those of the first opening portion 11.

An example of a material for the substrate layer 6 includes an insulator that is stretchable. Examples of the material include resins such as polyurethane resin.

The fracture elongation of the substrate layer 6 is, for example, 100% or more, preferably 200% or more, more preferably 300% or more, and for example, 2000% or less. When the fracture elongation is the above-described lower limit or more, the material for the substrate layer 6 is excellently stretchable.

The wire layer 7 is, for example, embedded in the second groove 12. To be more specific, the wire layer 7 is embedded in a one-side portion in the thickness direction of the substrate layer 6 so that the one-side surface in the thickness direction thereof is exposed from the substrate layer 6. The one-side surface in the thickness direction of the wire layer 7, along with the one-side surface in the thickness direction of the substrate layer 6 and the electronic component 3, forms the one-side surface in the thickness direction of the substrate 2.

The wire layer 7 has a wire pattern that connects the connecting portion 9 to the electronic component 3 (described later). The wire layer 7 includes a terminal for a component (not shown) to be used for electrical connection to the electronic component 3.

A width (line width) of the wire layer 7 is set within a range that does not interrupt the stretchability of the substrate layer 6, and is, for example, 2000 μm or less, preferably 500 μm or less, and for example, 50 μm or more, preferably 200 μm or more.

Examples of a material for the wire layer 7 include conductors such as copper, nickel, and gold, and an alloy thereof. As the material for the wire layer 7, preferably, copper is used.

Figure 4:
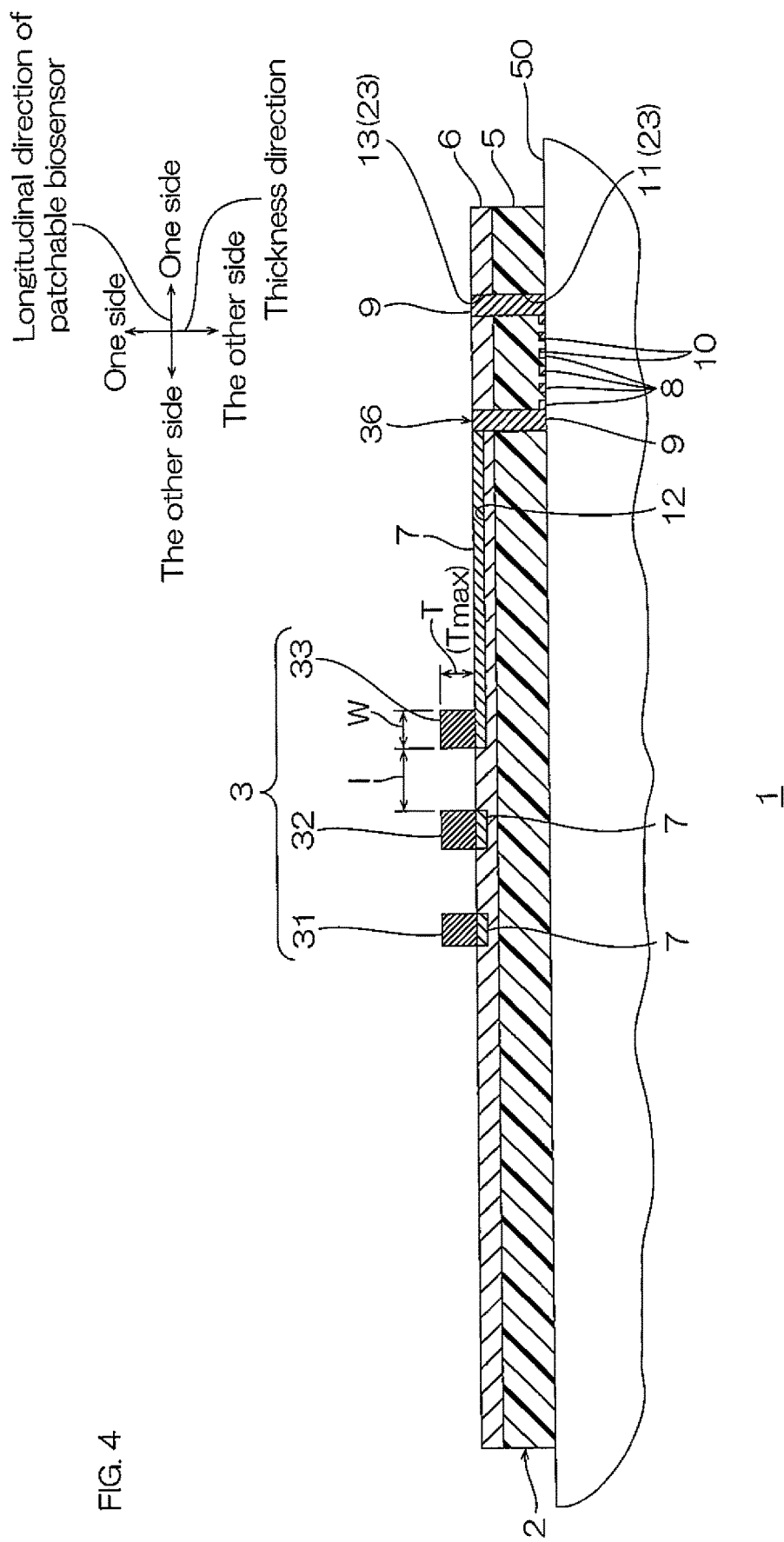
FIG. 4 shows a side cross-sectional view when the patchable biosensor shown in FIG. 2 is patched to the skin.

As shown in FIG. 4, the probe 8 is an electrode (bioelectrode) that senses an electrical signal, temperature, vibration, perspiration, and metabolite from a living body by being brought into contact with the skin 50 when the pressure-sensitive adhesive layer 5 is patched to the skin 50. The probe 8 is embedded in the pressure-sensitive adhesive layer 5 so as to be exposed from the other-side surface in the thickness direction of the pressure-sensitive adhesive layer 5. That is, the probe 8 is embedded in the first groove 10 in the pressure-sensitive adhesive layer 5 at the inside of the first opening portion 11. The probe 8 is disposed on the other-side surface in the thickness direction of the pressure-sensitive adhesive layer 5 that forms the first groove 10. The probe 8, along with the pressure-sensitive adhesive layer 5, forms the other-side surface in the thickness direction of the substrate 2. The probe 8 has a net shape, preferably a generally grid shape (or a generally mesh shape) when viewed from the top. As shown in FIG. 8, of the side surfaces of the probe 8, the outer-side surface that is positioned at the outermost side forms a phantom circle going through those when viewed from the top. As a material for the probe 8, the material illustrated in the wire layer 7 (to be specific, conductor) is used. A size of the outer shape of the probe 8 is set so that a phantom circle going through an outer-side surface 22 is overlapped with an inner peripheral surface defining the first opening portion 11 when viewed from the top.

As shown in FIGS. 1 and 2, the connecting portion 9 is provided corresponding to the second opening portion 13 and the first opening portion 11, and has the same shape as that of those. The connecting portion 9 passes through (goes through) the substrate layer 6 and the pressure-sensitive adhesive layer 5 in the thickness direction, and fills the second opening portion 13 and the first opening portion 11. As shown in FIG. 8B, the connecting portion 9 has an endless shape when viewed from the top along the outer-side surface 22 of the probe 8. To be specific, the connecting portion 9 has a generally cylindrical shape in which an axis line thereof extends in the thickness direction (is along the phantom circle going through the outer-side surface 22).

The inner-side surface of the connecting portion 9 is in contact with the outer-side surface 22 of the probe 8. The connecting portion 9 pressure-sensitively adheres to the pressure-sensitive adhesive layer 5 at the outside of the first opening portion 11 and the pressure-sensitive adhesive layer 5 at the inside of the first opening portion 11. The connecting portion 9 is in contact with the substrate layer 6 at the outside of the second opening portion 13 and the substrate layer 6 at the inside of the second opening portion 13.

The one-side surface in the thickness direction of the connecting portion 9 is flush with the one-side surface in the thickness direction of the substrate layer 6. The other-side surface in the thickness direction of the connecting portion 9 is flush with the other-side surface in the thickness direction of the pressure-sensitive adhesive layer 5.

As shown in FIG. 1, of the two connecting portions 9, the connecting portion 9 that is positioned at one side in the longitudinal direction is continuous to one end portion in the longitudinal direction of the wire layer 7 that is positioned at one side in the longitudinal direction in one end portion in the thickness direction thereof. The connecting portion 9 that is positioned at the other side in the longitudinal direction is continuous to the other end edge in the longitudinal direction of the wire layer 7 that is positioned at the other side in the longitudinal direction in one end portion in the thickness direction thereof. That is, the connecting portion 9 is electrically connected to the wire layer 7.

In this manner, the connecting portion 9 electrically connects the wire layer 7 to the probe 8.

Examples of a material for the connecting portion 9 include metal and electrically conductive resin (including electrically conductive polymer). Preferably, an electrically conductive resin or the like is used.

The connecting portion 9 and the wire layer 7 configure the circuit portion 36 that electrically connects the probe 8 to the electronic component 3. That is, the circuit portion 36 includes the wire layer 7 that is disposed on the one-side surface in the thickness direction of the substrate 2 and the connecting portion 9 that goes through the substrate 2 in the thickness direction. Preferably, the circuit portion 36 consists of only the wire layer 7 and the connecting portion 9.

Examples of the electronic component 3 include logic ICs such as analog front end, microcomputer, and memory for being processed and memorized as an electrical signal from a living body obtained by the probe 8; furthermore, transmitters such as communication IC for converting the electrical signal to an electric wave and wirelessly transmitting the electric wave to an external receiver; and furthermore, interposers.

As the electronic component 3, the above-described illustrations are appropriately used alone or in combination of two or more.

The electronic component 3 is disposed in one portion in the short-length direction in the central portion 46 in the longitudinal direction of the substrate 2. The plurality of (for example, three) electronic components 3 are disposed in alignment at spaced intervals to each other in the longitudinal direction of the substrate 2. To be specific, the electronic component 3 includes a first component 31, a second component 32, and a third component 33, and these are sequentially disposed from the other side toward one side in the longitudinal direction of the substrate 2. For example, the first component 31 is the analog front end, the second component 32 is the memory, and the third component 33 is the communication IC.

Each of the plurality of electronic components 3 extends in a longitudinal direction LD of the electronic component 3. The longitudinal direction LD of the electronic component 3 crosses the short-length direction of the substrate 2 and, to be specific, is perpendicular to the short-length direction of the substrate 2. To be specific, each of the plurality of electronic components 3 has a generally rectangular shape when viewed from the top extending long along the short-length direction of the substrate 2.

The plurality of electronic components 3 are overlapped with each other when projected in the longitudinal direction.

In the longitudinal directions LDs of the plurality of electronic components 3, one end edges 37 at the side toward one end edge in the short-length direction of the substrate 2 (one end edges in the longitudinal direction) are positioned at the same position when projected in the longitudinal direction of the substrate 2.

The electronic component 3 is disposed on the one-side surface in the thickness direction of the substrate 2. To be specific, the electronic component 3 is in contact with the one-side surface in the thickness direction of the substrate layer 6. The electronic component 3 has a generally rectangular flat plate shape when viewed from the cross-sectional view. A terminal (not shown) is provided on the other-side surface in the thickness direction of the electronic component 3. The terminal (not shown) of the electronic component 3 is electrically connected to a terminal for a component (not shown) of the wire layer 7.

The electronic component 3 is, for example, hard compared to the pressure-sensitive adhesive layer 5 and the substrate layer 6. Thus, an example of a material for the electronic component 3 includes a hard material. An example thereof includes a silicon-based inorganic material.

A length L in the longitudinal direction LD of the electronic component 3 is not particularly limited as long as it is above the above-described width W. For example, a ratio (L/W) of the length L in the longitudinal direction to the width W is set so as to be, for example, above 1, preferably 1.2 or more, more preferably 1.5 or more, and for example, 10 or less. The length L of the electronic component 3 signifies the length in the short-length direction of the substrate 2.

A thickness T of the electronic component 3 is, for example, 20 μm or more, preferably 50 μm or more, and for example, 3000 μm or less, preferably 1000 μm or less.

The maximum thickness Tmax of the electronic components 3 that are next to each other is, for example, 20 μm or more, preferably 50 μm or more, and for example, 3000 μm or less, preferably 1000 μm or less. The maximum thickness Tmax signifies the thickness of the electronic component 3 that is thicker in a case where the two electronic components 3 each of which has a different thickness are next to each other.

A gap I between the electronic components 3 that are next to each other is, for example, 40 μm or more, preferably 100 μm or more, and for example, 6000 μm or less, preferably 2000 μm or less. The gap I corresponds to a distance in the short-length direction of the substrate 2 between the electronic components 3 that are next to each other.

A ratio (I/Tmax) of the gap I between the two electronic components 3 that are next to each other to the maximum thickness Tmax of the two electronic components 3 is, for example, 2 or more, preferably 2.5 or more, more preferably 3 or more, and for example, 4 or less.

When the above-described ratio (I/Tmax) is the above-described lower limit or more, the plurality of electronic components 3 can be disposed in saving space (at high density).

Meanwhile, when the above-described ratio (I/Tmax) is the above-described lower limit or more, in a case where the patchable biosensor 1 is patched to the skin 50, contact of the two electronic components 3 with each other is effectively suppressed, and damage to the electronic component 3 can be effectively suppressed.

The width W of the electronic component 3 is a length of a direction perpendicular to the longitudinal direction LD of the electronic component 3. The width W of the electronic component 3 corresponds to the length in the longitudinal direction of the substrate 2, and to be specific, is, for example, 5000 μm or less, preferably 4000 μm or less, more preferably 3000 μm or less, and for example, 1000 μm or more. When the width W is the above-described upper limit or less, in a case where the substrate 2 is patched to the skin 50, the damage at the time of applying the stress to the electronic component 3 can be effectively suppressed.

As shown in FIG. 2, the patchable biosensor 1 includes a first release sheet 19 as one example of a release sheet. The first release sheet 19 forms the lowermost surface of the patchable biosensor 1. The first release sheet 19 is disposed on the other-side surface in the thickness direction of the substrate 2. The first release sheet 19 is a protecting sheet that covers the other-side surface in the thickness direction of the substrate 2 (pressure-sensitive adhesive surface of the pressure-sensitive adhesive layer 5) to be protected from damage, dust, or the like. The first release sheet 19 is a peelable sheet that is peeled from the substrate 2 along the longitudinal direction of the substrate 2 at the time of the use of the patchable biosensor 1 (ref: FIGS. 3B to 3D).

The first release sheet 19 has, for example, a generally flat plate shape extending in the longitudinal direction of the substrate 2. Examples of a material for the first release sheet 19 include resins (polymers) such as polyester (polyethylene terephthalate or the like) and polyolefin (polypropylene or the like), and metals such as aluminum and stainless steel. As the material for the first release sheet 19, in view of stretchability, preferably, a resin is used.

Next, a method for producing the patchable biosensor 1 is described with reference to FIGS. 5A to 8.

In this method, first, the substrate 2 is prepared in conformity with FIGS. 5A to 5D.

To prepare the substrate 2, first, as shown in FIG. 5A, the substrate layer 6 and the wire layer 7 are prepared. The substrate layer 6 and the wire layer 7 are prepared so that the wire layer 7 is embedded in the second groove 12 by the method described in, for example, Japanese Unexamined Patent Publications No. 2017-22236 and No. 2017-22237.

Next, as shown in FIG. 5B, the pressure-sensitive adhesive layer 5 is disposed on the other-side surface in the thickness direction of the substrate layer 6. To dispose the pressure-sensitive adhesive layer 5, for example, first, an application liquid containing the material for the pressure-sensitive adhesive layer 5 is prepared and subsequently, the application liquid is applied to the one-side surface in the thickness direction of the first release sheet 19 to be then dried by heating. In this manner, the pressure-sensitive adhesive layer 5 is disposed on the one-side surface in the thickness direction of the first release sheet 19.

Next, the pressure-sensitive adhesive layer 5 is attached to the substrate layer 6 by, for example, laminator or the like. To be specific, the one-side surface in the thickness direction of the pressure-sensitive adhesive layer 5 is brought into contact with the other-side surface in the thickness direction of the substrate layer 6.

At this point, each of the substrate layer 6 and the pressure-sensitive adhesive layer 5 does not have the second opening portion 13 and the first opening portion 11 (an opening portion 23) (ref: FIG. 5C), respectively.

As shown in FIG. 5C, next, the opening portion 23 is formed in the substrate layer 6 and the pressure-sensitive adhesive layer 5.

The opening portion 23 passes through the substrate layer 6 and the pressure-sensitive adhesive layer 5. The opening portion 23 is a hole (through hole) in a generally circular shape when viewed from the top defined by an outer peripheral surface that defines the second opening portion 13 and the outer peripheral surface that defines the first opening portion 11. The opening portion 23 has an opening toward one side in the thickness direction. Meanwhile, the lower end of the opening portion 23 is sealed by the first release sheet 19.

To form the opening portion 23, the pressure-sensitive adhesive layer 5 and the substrate layer 6 are, for example, subjected to punching and half etching.

Next, a probe member 18 is prepared to be fitted into the inside of the opening portion 23.

Figure 6:
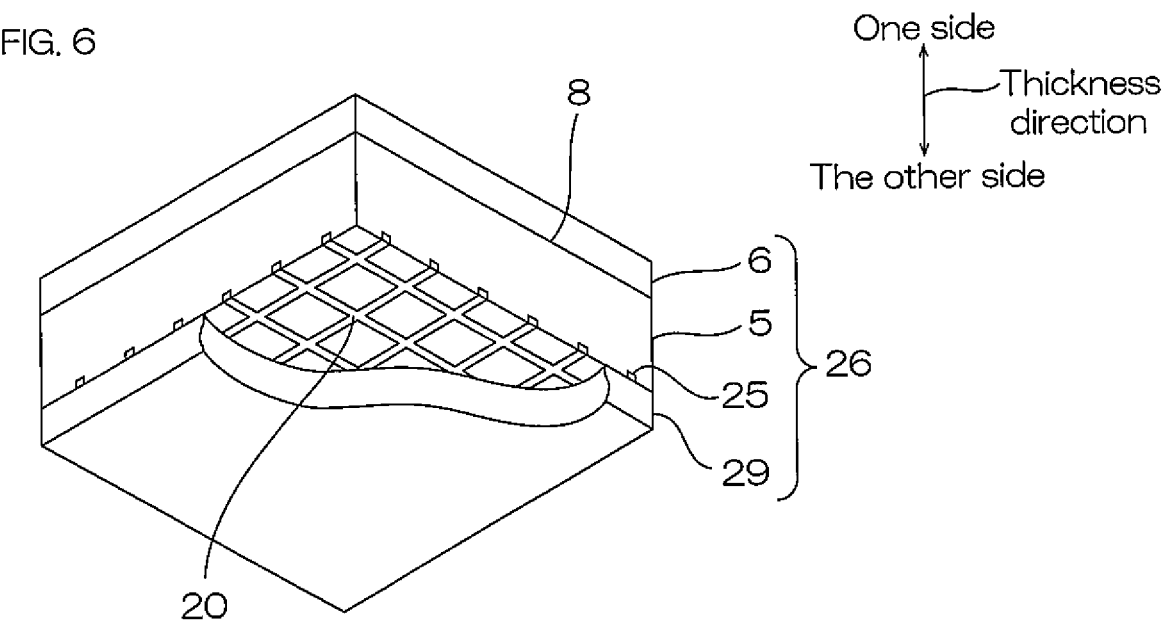
FIG. 6 shows a perspective view when a probe-including sheet is viewed from below, and shows a perspective view of cutting out a portion of a second release sheet.

To prepare the probe member 18, first, as shown in FIG. 6, a probe-including sheet 26 is prepared.

The probe-including sheet 26 includes a second release sheet 29, a probe pattern 25 that is formed at one side in the thickness direction of the second release sheet 29, the pressure-sensitive adhesive layer 5 that is formed at one side in the thickness direction of the second release sheet 29 and embeds the probe pattern 25, and the substrate layer 6 that is disposed on the one-side surface in the thickness direction of the pressure-sensitive adhesive layer 5.

The second release sheet 29 has the same structure as that of the above-described first release sheet 19.

The probe pattern 25 has the same pattern shape as that of the probe 8. A material for the probe pattern 25 is the same as that for the probe 8. The probe pattern 25 has the plane area that is larger than the phantom circle going through the outer-side surface 22 of the probe 8.

Each of the pressure-sensitive adhesive layer 5 and the substrate layer 6 in the probe-including sheet 26 has the same structure as that of the pressure-sensitive adhesive layer 5 and that of the substrate layer 6 described above.

The probe-including sheet 26 is prepared by the method described in, for example, Japanese Unexamined Patent Publications No. 2017-22236 and No. 2017-22237.

Next, as shown in FIG. 7, a cutting line 27 in a generally circular shape when viewed from the top is formed in the probe pattern 25, the pressure-sensitive adhesive layer 5, and the substrate layer 6. The cutting line 27 is formed by, for example, punching or the like. The cutting line 27 divides the probe pattern 25, the pressure-sensitive adhesive layer 5, and the substrate layer 6 at the inside and the outside thereof, and is not formed in the second release sheet 29. The size of the cutting line 27 is the same as the inner size of the first opening portion 11 and the second opening portion 13. That is, the cutting line 27 coincides with the phantom circle going through the outer-side surface 22.

The probe member 18 is formed by forming of the cutting line 27.

In the probe member 18, the outer-side surface 22 of the probe 8 is flush with the outer-side surface of the pressure-sensitive adhesive layer 5. In the probe member 18, the outer-side surface 22 is exposed from the outer-side surface of the pressure-sensitive adhesive layer 5 outwardly in a radial direction.

Subsequently, as shown by an arrow of FIG. 7, the probe member 18 is pulled up from the second release sheet 29. To be specific, the other-side surface in the thickness direction of the probe member 18 is peeled from the second release sheet 29.

Thereafter, as shown by the arrow of FIG. 5C, the probe member 18 is fitted into the inside of the opening portion 23.

At this time, the pressure-sensitive adhesive layer 5, the substrate layer 6, and the probe 8 of the probe member 18 are spaced apart from the pressure-sensitive adhesive layer 5 and the substrate layer 6 around the opening portion 23. That is, the probe member 18 is fitted into the inside of the opening portion 23 so as to form the second opening portion 13 and the first opening portion 11.

Thereafter, as shown by FIG. 5D, the connecting portion 9 is provided at the inside of the second opening portion 13 and the first opening portion 11.

To be specific, when the material for the connecting portion 9 is an electrically conductive resin composition, the electrically conductive resin composition (electrically conductive composition liquid) is poured into (or applied to) the second opening portion 13 and the first opening portion 11. Thereafter, the electrically conductive resin composition (electrically conductive composition liquid) is heated and a solvent is removed, and a binder resin is cross-linked by a cross-linking agent.

In this manner, a laminate 30 for a biosensor including the substrate 2 and the first release sheet 19 is produced. The laminate 30 for a biosensor does not include the electronic component 3 (furthermore, a cell 45), that is, the laminate 30 for a biosensor is not the patchable biosensor 1 and is an intermediate component for producing the patchable biosensor 1.

As shown in FIG. 2, thereafter, the plurality of electronic components 3 are mounted on the laminate 30 for a biosensor. To be specific, a terminal (not shown) of the electronic component 3 is brought into contact with a terminal for a component (not shown) in the wire layer 7, and the other-side surface in the thickness direction of the electronic component 3 is brought into contact with the one-side surface in the thickness direction of the substrate layer 6.

In this manner, the patchable biosensor 1 including the substrate 2, the electronic component 3, and the first release sheet 19 is produced.

The patchable biosensor 1 preferably consists of only the substrate 2, the electronic component 3, and the first release sheet 19.

Next, the usage of the patchable biosensor 1 is described with reference to FIGS. 3A to 4.

To use the patchable biosensor 1, first, as shown by a phantom line of FIG. 1, the cell 45 is mounted on the patchable biosensor 1.

The cell 45 has a generally flat plate (box) shape extending in a plane direction. The cell 45 has a terminal (not shown) that is provided on the other-side surface in the thickness direction thereof.

To mount the cell 45 on the patchable biosensor 1, a terminal (not shown) of the cell 45 is electrically connected to a terminal for a cell (not shown) of the wire layer 7. At this time, the other-side surface in the thickness direction of the cell 45 is brought into contact with the one-side surface in the thickness direction of the substrate layer 6.

Next, the first release sheet 19 (ref: the arrow and the phantom line of FIG. 3D) is peeled from the substrate 2, and the substrate 2 is patched to the skin 50.

As shown by the phantom line and the arrow of FIG. 3A, for example, first, one end edge in the longitudinal direction of the first release sheet 19 (portion facing one end edge in the longitudinal direction of the substrate 2 in the first release sheet 19) is peeled from the substrate 2, and as shown in FIG. 3B, while holding the one end edge, the one-side portion in the longitudinal direction of the first release sheet 19 is peeled from the one-side portion in the longitudinal direction of the substrate 2. In this manner, the one-side portion in the longitudinal direction of the other-side surface (pressure-sensitive adhesive surface) in the thickness direction of the substrate 2 is exposed toward the other side in the thickness direction.

Subsequently, as shown in FIGS. 3C and 3D, the other-side surface (pressure-sensitive adhesive surface) in the thickness direction of the substrate 2 pressure-sensitively adheres to the surface of the skin 50.

Thereafter, as shown by the arrow of FIG. 3D, and FIG. 4, an other-side portion in the longitudinal direction of the first release sheet 19 is peeled from the other-side portion in the longitudinal direction of the substrate 2, and the other-side portion in the longitudinal direction of the substrate 2 is exposed. Immediately after this, the portion pressure-sensitively adheres to the surface of the skin 50. In this manner, the first release sheet 19 is removed from the patchable biosensor 1, and at the same time, the entire other-side surface (pressure-sensitive adhesive surface) in the thickness direction of the substrate 2 is patched to the surface of the skin 50.

Thereafter, a living body is sensed by the probe 8, the circuit portion 36 (the connecting portion 9 and the wire layer 7), and the electronic component 3.

To be specific, the probe 8 senses as the electrical signal from the living body, and the electrical signal sensed by the probe 8 is input into the electronic component 3 via the connecting portion 9 and the wire layer 7. The electronic component 3 processes the electrical signal and memorizes it as information based on an electric power supplied from the cell 45. Furthermore, if necessary, the electrical signal is converted into an electric wave to be wirelessly transmitted to an external receiver.

To be more specific, the operation of the first component 31, the second component 32, and the third component 33 in the electronic component 3 is described in the following. When the patchable biosensor 1 is a patchable electrocardiograph (described later), a potential change of the heart obtained by the probe 8 is converted into digital data in the first component 31 that is the analog front end, and records the potential change of the heart in the second component 32 that is the memory. As one example, the second component 32 records the potential change of the heart of 16 bit and the data rate of 1 kHz. Also, the third component 33 that is the communication IC wirelessly transmits the signal obtained by the probe 8 to the outside.

After the above-described operation (that is, after the sensing of the living body by the patchable biosensor 1), the patchable biosensor 1 is removed from the skin 50, and the recorded data is taken out from the second component 32 to be analyzed. Thereafter, the second component 32 (furthermore, the first component 31 and the third component 33 as needed) is reused.

As shown in FIGS. 10 and 11, in Comparative Example 1 in which the longitudinal direction LD of the electronic component 3 is along the longitudinal direction of the substrate 2, when the substrate 2 is attempted to be patched to the skin 50 along the longitudinal direction thereof, the substrate 2 is deformed along the longitudinal direction thereof, and in this way, a large stress F is applied to the above-described electronic component 3. Thus, as shown in FIG. 11B, the damage (crack or the like) to the electronic component 3 occurs by the stress F.

In the patchable biosensor 1, however, as shown in FIG. 3D, when the substrate 2 is patched to the skin 50 along the longitudinal direction thereof, and the substrate 2 is deformed along the longitudinal direction thereof, the longitudinal direction LD of the electronic component 3 crosses the longitudinal direction of the substrate 2, so that the stress applied to the electronic component 3 can be reduced. Thus, when the substrate 2 is patched to the skin 50, the damage to the electronic component 3 caused by the above-described stress can be suppressed.

Furthermore, the longitudinal direction LD of the electronic component 3 is perpendicular to the longitudinal direction of the substrate 2, so that the stress applied to the electronic component 3 can be furthermore surely reduced.

As shown in FIG. 11, when the first release sheet 19 is peeled along the longitudinal direction of the substate 2, the substrate 2 is stretchable, so that the deformation easily occurs.

As described above, however, in the patchable biosensor 1, the longitudinal direction LD of the electronic component 3 crosses the longitudinal direction of the substrate 2, so that when the first release sheet 19 is peeled from the substrate 2, the stress applied to the electronic component 3 can be reduced. Thus, when the substrate 2 is patched to the skin 50, the damage to the electronic component 3 can be furthermore surely suppressed.

As shown in FIGS. 12 and 13, there may be a case where the plurality of electronic components 3 having the longitudinal directions LDs along the longitudinal direction of the substrate 2 and disposed next to each other in the longitudinal direction of the substrate 2 are brought into contact with each other by the above-described deformation along the longitudinal direction of the substrate 2, and are damaged caused by the contact (Comparative Example 2). To be specific, the damage caused by the contact of the first component 31 with the second component 32, and the contact of the second component 32 with the third component 33 is assumed.

In the patchable biosensor 1, however, as shown in FIG. 1, the longitudinal direction LD of the electronic component 3 crosses the longitudinal direction of the substrate 2, so that the above-described occurrence of the contact is suppressed, and the damage to the electronic component 3 can be suppressed.

In the patchable biosensor 1, when the ratio (I/Tmax) of the gap I between the two electronic components 3 to the maximum thickness Tmax of the electronic component 3 is 2 or more, the contact of the two electronic components 3 that are next to each other with each other is effectively suppressed, and the damage to the electronic component 3 can be effectively suppressed.

In the patchable biosensor 1, at least one selected from the group consisting of the analog front end, the microcomputer, the memory, the interposer, and the chip is hard or fragile, and thus, the electronic component 3 may be damaged when the stress is applied thereto.

As described above, however, in the patchable biosensor 1, the longitudinal direction LD of the electronic component 3 crosses the longitudinal direction of the substrate 2, so that the stress applied to the electronic component 3 can be reduced.

Furthermore, the electronic component 3 includes the first component 31 that is the analog front end, the second component 32 that is the memory, and the third component 33 that is the communication IC, so that sensing performance of the patchable biosensor 1 can be improved by the above-described operation in the electronic component 3.

The patchable biosensor 1 is not particularly limited as long as it is, for example, a device that is capable of monitoring a state of a living body by sensing an electrical signal from the living body. To be specific, examples of the patchable biosensor 1 include patchable electrocardiograph, patchable electroencephalograph, patchable hemomanometer, patchable pulsimeter, patchable electromyograph, patchable thermometer, and patchable accelerometer. These devices may be an individual device, or a plurality of these may be installed in one device.

The patchable biosensor 1 is preferably used as a patchable electrocardiograph. In the patchable electrocardiograph, the probe 8 senses an action potential of the heart as the electrical signal.

The living body includes a human body and a living being other than the human body. Preferably, a human body is used.

MODIFIED EXAMPLES

In the modified examples, the same reference numerals are provided for members and steps corresponding to each of those in the one embodiment, and their detailed description is omitted. Furthermore, in the modified examples, the same function and effect as that of the one embodiment can be achieved unless otherwise specified.

As shown in FIG. 4, the patchable biosensor 1 can also include (only) the substrate 2 and the electronic component 3 without including the first release sheet 19.

As shown in FIG. 2, preferably, the patchable biosensor 1 includes the first release sheet 19, the substrate 2, and the electronic component 3. The pressure-sensitive adhesive surface of the substrate 2 can be protected from the damage, the dust, or the like by the first release sheet 19. Meanwhile, as shown in FIG. 3B, when the first release sheet 19 is peeled from the substrate 2 along the longitudinal direction of the substrate 2, the deformation of the substrate 2 easily occurs.

As described above, however, in the patchable biosensor 1, the longitudinal direction LD of the electronic component 3 crosses the longitudinal direction of the substrate 2, so that when the first release sheet 19 is peeled from the substrate 2, the stress applied to the electronic component 3 can be reduced.

The longitudinal direction LD of the electronic component 3 may cross the longitudinal direction of the substrate 2. That is, though not shown, the longitudinal direction LD of the electronic component 3 is not perpendicular to the longitudinal direction of the substrate 2, and may cross the longitudinal direction of the substrate 2. To be specific, as shown in FIG. 9A, the longitudinal directions LDs of the plurality of electronic components 3 incline with respect to the longitudinal direction of the substrate 2. An angle made between the longitudinal direction LD of the electronic component 3 and the longitudinal direction of the substrate 2 is, for example, above 0 degree, furthermore 30 degrees or more, and for example, below 90 degrees, furthermore, below 60 degrees.

Furthermore, the longitudinal direction LD that crosses (is perpendicular to) the longitudinal direction of the substrate 2 may be included in the electronic component 3. For example, of the plurality of electronic components 3, one may have the longitudinal direction LD that crosses (is perpendicular to) the longitudinal direction of the substrate 2, and another may also have the longitudinal direction LD along the longitudinal direction of the substrate 2.

To be specific, of the plurality of electronic components 3, for example, the longitudinal directions LDs of the one or more electronic components 3 cross (are perpendicular to) the longitudinal direction of the substrate 2, preferably, the longitudinal directions LDs of a half or more of the electronic components 3 cross (are perpendicular to) the longitudinal direction of the substrate 2, more preferably, the longitudinal directions LDs of 80% or more of the electronic components 3 cross (are perpendicular to) the longitudinal direction of the substrate 2, further more preferably, the longitudinal directions LDs of all of the electronic components 3 cross (are perpendicular to) the longitudinal direction of the substrate 2.

The arrangement of the plurality of electronic components 3 is not limited to the description above, and for example, the arrangement shown in FIGS. 9B to 9H can be also used.

For example, as shown in FIG. 9B, in the modified example, the plurality of electronic components 3 (the first component 31, the second component 32, and the third component 33) are disposed at spaced intervals to each other in the short-length direction of the substrate 2.

As shown in FIG. 9C, the plurality of electronic components 3 are disposed in the central portion in the short-length direction of the substrate 2. Each of both end edges in the short-length direction of the substrate 2 extends linearly along the longitudinal direction of the substrate 2 over the central portion 46 in the longitudinal direction and both end portions in the longitudinal direction.

As shown in FIGS. 9D and 9E, the plurality of electronic components 3 are disposed in alignment at spaced intervals to each other in both directions of the longitudinal direction and the short-length direction of the substrate 2. To be specific, in the modified example shown in FIG. 9D, the electronic component 3 includes the first component 31, the second component 32, and the third component 33 that are disposed at spaced intervals to each other in the longitudinal direction, and a fourth component 34 and a fifth component 35 that are disposed at spaced intervals to each other at both sides in the short-length direction of the second component 32.

In the modified example shown in FIG. 9E, the first component 31 and the second component 32 are disposed at spaced intervals to each other in the longitudinal direction of the substrate 2, and the third component 33 and the fourth component 34 are disposed at spaced intervals to each other in the longitudinal direction of the substrate 2. Each of the third component 33 and the fourth component 34 is disposed to face each of the first component 31 and the second component 32 at spaced intervals thereto at the other side in the short-length direction.

As shown in FIGS. 9F to 9H, in the modified example, the plurality of electronic components 3 are displaced from each other. For example, in the modified example shown in FIG. 9F, when projected in the longitudinal direction of the substrate 2, the first component 31 and the third component 33 are displaced from the second component 32 and the fourth component 34, and are not overlapped with them.

In the modified example shown in FIG. 9G, when projected in the longitudinal direction of the substrate 2, a portion of the first component 31 (the other-side portion in the longitudinal direction LD of the electronic component 3) is overlapped with the second component 32, and a remaining portion of the first component 31 (one-side portion in the longitudinal direction LD of the electronic component 3) is not overlapped with the second component 32. Also, when projected in the longitudinal direction of the substrate 2, a portion of the second component 32 (the other-side portion in the longitudinal direction LD of the electronic component 3) is overlapped with the third component 33, and a remaining portion of the second component 32 (one-side portion in the longitudinal direction LD of the electronic component 3) is not overlapped with the third component 33.

Furthermore, as shown in FIG. 9H, when projected in the longitudinal direction of the substrate 2, the first component 31, the second component 32, the third component 33, and the fourth component 34 are sequentially disposed from one side toward the other side in the short-length direction of the substrate 2, and when projected in the short-length direction of the substrate 2, the first component 31, the second component 32, the third component 33, and the fourth component 34 are sequentially disposed from the other side toward one side in the longitudinal direction of the substrate 2.

Of the modified examples of FIGS. 9A to 9H, preferably, the modified examples of FIGS. 9B, 9D, 9F, 9G, and 9H are used, more preferably, the modified examples of FIGS. 9B, 9F, and 9H are used.

In the modified examples of FIGS. 9B, 9D, 9F, 9G, and 9H, when projected in the longitudinal direction of the substrate 2, a portion that is not overlapped with each other exists, so that the contact of at least the above-described portions with each other caused by the deformation when the substrate 2 is patched to the skin 50 can be effectively suppressed.

In the modified examples of FIGS. 9B, 9F, and 9H, when projected in the longitudinal direction of the substrate 2, a portion that is overlapped with each other does not exist, so that the contact of the electronic components 3 with each other can be prevented.

While the illustrative embodiments of the present invention are provided in the above description, such is for illustrative purpose only and it is not to be construed as limiting the scope of the present invention. Modification and variation of the present invention that will be obvious to those skilled in the art is to be covered by the following claims.

INDUSTRIAL APPLICABILITY

The patchable biosensor of the present invention is, for example, used for a patchable electrocardiograph, a patchable electroencephalograph, a patchable hemomanometer, a patchable pulsimeter, a patchable electromyograph, a patchable thermometer, a patchable accelerometer, or the like.

DESCRIPTION OF REFERENCE NUMERALS

1 Patchable biosensor
2 Substrate
3 Electronic component
19 First release sheet
31 Analog front end (one example of first component)
32 Memory (one example of second component)
33 Communication IC (one example of third component)
34 Fourth component
35 Fifth component
50 Skin
LD Longitudinal direction of electronic component
I Gap between electronic components
Tmax Maximum thickness of electronic components next to each other

The invention claimed is:
1. A patchable biosensor comprising:
a substrate extending in a longitudinal direction and being stretchable for being patched to a surface of a living body and
an electronic component disposed on a one-side surface in a thickness direction of the substrate and extending in the longitudinal direction, wherein
the longitudinal direction of the electronic component crosses the longitudinal direction of the substrate,
the longitudinal direction of the electronic component is perpendicular to the longitudinal direction of the substrate,
the electronic component has a width W of 3000 μm or less
the electronic component includes at least two electronic components disposed next to each other along the longitudinal direction of the substrate, and
a ratio (I/Tmax) of a gap I between the two electronic components in the longitudinal direction of the substrate to the maximum thickness Tmax of the electronic component is 2 or more.
2. The patchable biosensor according to claim 1 further comprising:
a release sheet disposed on an other-side surface in the thickness direction of the substrate and for being peeled along the longitudinal direction of the substrate.

3. The patchable biosensor according to claim 1, wherein at least one of the at least two electronic components is at least one selected from the group consisting of an analog front end, a microcomputer, a memory, an interposer, and a chip.

* * * * *